United States Patent [19]

Bokerman et al.

[11] Patent Number: 5,120,520
[45] Date of Patent: Jun. 9, 1992

[54] SILANE PRODUCTS FROM REACTION OF SOLID SILICON MONOXIDE WITH AROMATIC HALIDES

[75] Inventors: Gary N. Bokerman; John P. Cannady, both of Madison, Ind.; Charles S. Kuivila, LaGrange, Ky.

[73] Assignee: Dow Corning Corporation, Midland, Mich.

[21] Appl. No.: 700,277

[22] Filed: May 15, 1991

[51] Int. Cl.$^5$ ............................................. C01B 33/107
[52] U.S. Cl. .................... 423/342; 252/182.3; 423/347; 556/472
[58] Field of Search ............... 423/342, 347, 341, 344; 252/182.3; 556/472

[56] References Cited

U.S. PATENT DOCUMENTS

| | | | |
|---|---|---|---|
| 3,660,448 | 5/1972 | Schaschel | 556/410 |
| 3,660,449 | 5/1972 | Schaschel | 556/430 |
| 3,660,450 | 5/1972 | Timms | 556/434 |
| 3,660,451 | 5/1972 | Schaschel | 556/452 |
| 3,661,961 | 5/1972 | Schaschel | 556/451 |
| 4,585,646 | 4/1986 | Gomberg | 423/658.2 |

Primary Examiner—Robert Kunemund
Assistant Examiner—Ken Horton
Attorney, Agent, or Firm—William F. Boley

[57] ABSTRACT

The described invention is a process for preparing silanes from the reaction of solid silicon monoxide with aromatic halides. The solid silicon monoxide is reacted with the aromatic halide in the presence of a catalyst which can increase the conversion of silicon monoxide to silanes, and partially select for arylsilane products. The process may employ an activation step in which the solid silicon monoxide is activated by heating in an inert atmosphere. Activation of the solid silicon monoxide can increase silicon conversion and increase selectivity for arylsilane products.

22 Claims, No Drawings

SILANE PRODUCTS FROM REACTION OF SOLID SILICON MONOXIDE WITH AROMATIC HALIDES

BACKGROUND OF INVENTION

The present invention is a process for preparing silanes by the reaction of solid silicon monoxide with aromatic halides, in the presence of a catalyst. The described catalysts can increase conversion of the silicon monoxide and alter the product selectivity of the described processes. Product selectivity can be further altered by an activation step comprising the heating of the solid silicon monoxide in an inert atmosphere.

Silanes are primarily produced by the direct reaction of silicon metal with organic halides or hydrogen halides, as first disclosed by Rochow and his co-workers in the 1940's. A significant portion of the cost of this process is the cost of the silicon metal used as a feed material. Silicon metal is typically produced in an electric-arc furnace by the carbothermic reduction of silicon dioxide. This process requires high temperature and high energy consumption, which is reflected in the cost of silicon metal.

Silicon monoxide can be produced at a lower temperature than silicon and, thus, may serve as a less expensive raw material for the production of silanes. The instant invention describes a process whereby potentially less expensive solid silicon monoxide can be reacted with aromatic halides to produce silanes, especially arylsilanes.

Schaschel, in a series of patents, describes a process for preparing organosilicon polymers by reacting silicon monoxide with organic compounds. The methods of the described invention involved preparation of silicon monoxide vapors from solid silicon monoxide by heating the same under vacuum to about 1200° C. to 1300° C.; mixing in a chamber having cooled walls the gaseous silicon monoxide formed thereby, with an excess of a volatile organic compound to form a mixture; and condensing the mixture to obtain the organosilicon polymer. The reaction is reported to occur on the cold surface of the chamber to form the polymer thereupon.

The reactions of organic compounds taught by Schaschel are: Schaschel, U.S. Pat. No. 3,660,448, issued May 2, 1972, organic compounds containing active hydrogen atoms such as alcohols and amines; Schaschel, U.S. Pat. No. 3,660,449, issued May 2, 1972, organic compounds containing a triple bond such as acetylene; Schaschel, U.S. Pat. No. 3,660,451, issued May 2, 1972, organic monohalides such as 1-bromobutane; and Schaschel, U.S. Pat. No. 3,661,961, issued May 9, 1972, aliphatic hydrocarbons such as n-octane.

Timms, U.S. Pat. No. 3,660,450, issued May 2, 1972, teaches a process for reacting gaseous silicon monoxide with an aromatic compound containing at least one benzene nucleus, the compound having no triple bonds and no active hydrogen atoms. The described process is similar to that previously described for the Schaschel series of patents.

Gomberg, U.S. Pat. No. 4,585,646, issued Apr. 29, 1986, teaches a process where $Si_2OCl_6$ is irradiated to form solid SiO. The solid SiO is isolated and reacted at 500° C. with HCl. The process is reported to form tetrachlorosilane, water, and hydrogen gas. No SiH— products are produced. In addition, no activation process for the silicon monoxide or use of a catalyst is taught.

Kuivila et al., Co-Pending U.S. patent application Ser. No. 567,576, filed Aug. 15, 1990, discloses a process for preparing silanes and halosilanes from the reaction of solid silicon monoxide with hydrogen halides. Higher conversion of silicon monoxide to product silanes and altered distribution of the types of silanes produced are observed when the solid silicon monoxide is heat activated in an inert atmosphere prior to contact with the hydrogen halides. Conversion of silicon monoxide and selectivity for the type of silanes produced is also affected when a metal or metal salt catalyst is present during the reaction of unactivated or activated silicon monoxide.

Kuivila et al., Co-Pending U.S. patent application Ser. No. 576,908, filed Sep. 4, 1990, discloses a process for producing silane products from reaction of solid silicon monoxide with alkyl- and alkenyl-substituted halides. The solid silicon monoxide is reacted with the organic halide in the presence of a catalyst which can increase the conversion of silicon monoxide to silanes and partially select for the type of silanes produced. The process may employ an activation step in which the solid silicon monoxide is activated by heating in an inert atmosphere. Activation of the silicon monoxide was found to increase silicon conversion and alter the type of silanes produced.

SUMMARY OF INVENTION

The present invention is a process for preparing silanes by the reaction of solid silicon monoxide with aromatic halides. The solid silicon monoxide is reacted with the aromatic halide in the presence of a catalyst which can increase the conversion of silicon monoxide to silanes, and partially select for arylsilane products. The process may employ an activation step in which the solid silicon monoxide is activated by heating in an inert atmosphere. Activation of the solid silicon monoxide can increase silicon conversion and increase the selectivity of the process for arylsilane products.

DESCRIPTION OF INVENTION

A process for producing silanes by the reaction of solid silicon monoxide with aromatic halides is described. The process comprises:

(A) contacting solid silicon monoxide, an aromatic halide of formula $$RX,$$

where X is a halide and R is selected from a group consisting of aryl radicals, and a catalyst effective in facilitating reaction of the solid silicon monoxide with the aromatic halide; at a reaction temperature of 200° C. to 1200° C.; and (B) forming silanes of formula $$H_aR_bSiX_{4-a-b}$$

where a is an integer from 0 to 4, b is an integer from 0 to 4, a+b is an integer from 0 to 4, and R and X are as previously described.

The contacting of the solid silicon monoxide, aromatic halide, and catalyst can be effected in any standard reactor for effecting contact of gases with particulate solids. The process can be conducted, for example, in a fixed-bed reactor, a stirred-bed reactor, a vibrating-bed reactor, or a fluidized-bed reactor.

The source of solid silicon monoxide is not critical to the instant described process. However, a preferred source is solid silicon monoxide produced by the carbothermic reduction of silicon dioxide, since this source allows for potential energy savings incurred by not requiring the total reduction of silicon dioxide to silicon.

The solid silicon monoxide can be in any convenient particulate form, for example, chips, flakes, powder, or granules. A range of useful particle sizes is about 0.5 micron to 120 mesh. A preferred particle size range is about two micron to about 320 mesh. The term "about," is meant to include similar particle sizes which give comparable levels of silicon monoxide conversion and similar product selectivity.

In general the smaller the particle size of the solid silicon monoxide, the higher the conversion of silicon monoxide to silanes. The lower end of the particle size range is limited primarily by the ability to efficiently make and handle the particulate silicon monoxide. Silicon monoxide of particle size greater than that described will work in the instant process, however, conversion of silicon monoxide to silanes may be reduced.

The solid silicon monoxide is contacted with an aromatic halide of formula RX, where X is a halide and R is selected from a group consisting of aryl radicals. The aryl radical can be, for example, phenyl, tolyl, xylyl, and naphthyl radicals. The preferred aryl radical is the phenyl radical. The halide, X, can be, for example, bromide, chloride, fluoride, or iodide. The preferred halide is chloride. The preferred aromatic halide is chlorobenzene.

The silicon monoxide and aromatic halide are contacted in the presence of a catalyst effective in facilitating reaction of the solid silicon monoxide with the aromatic halide. By effective, it is meant chemical elements and compounds thereof which, in the presence of an aromatic halide, increase the conversion of silicon monoxide to silanes, increase the rate of conversion, or modify the distribution of silane products. Any or all of the aforementioned effects may be an indication of effectiveness of the catalyst.

Materials which are effective catalysts in the described processes are metal and metal compounds selected from the group consisting of: aluminum and aluminum compounds, antimony and antimony compounds, copper and copper compounds, cadmium and cadmium compounds, iron and inorganic iron compounds, manganese and manganese compounds, mercury and mercury compounds, nickel and nickel compounds, silver and silver compounds, tin and tin compounds, zinc and zinc compounds, phosphorous, metal phosphides, metal phosphorous alloys and mixtures thereof.

Preferred is a catalyst selected from a group consisting of aluminum and aluminum compounds, copper and copper compounds, silver and silver compounds, tin and tin compounds, zinc and zinc compounds and mixtures thereof. More preferred is when the catalyst is selected from a group consisting of Al, AgCl, CuCl and mixtures thereof. Even more preferred is when the catalyst is a mixture which results in the following final concentrations of metal and metal compounds in a silicon monoxide and catalyst composition: 15 to 25 weight percent CuCl, 1500 to 1800 ppm Al, and five to 10 weight percent AgCl.

A useful concentration of catalyst is considered to be three to 50 weight percent of the combined catalyst and silicon monoxide weight. Lower levels of catalyst may be used, but conversion of silicon monoxide may be reduced. Higher levels of catalyst may be used, which result in increased conversion of silicon monoxide, however, selectivity for arylhalosilanes may be decreased at these higher levels.

A preferred catalyst concentration is where the catalyst is present at 10 to 40 weight percent of the combined catalyst and silicon monoxide weight.

The catalyst can be in any convenient particulate form, such as powder, granule, flake or chip. The mixture can be formed by standard means for mixing particulate materials. For best results, it is preferred that the catalyst be distributed uniformly throughout the particulate silicon monoxide.

Increased conversion of solid silicon monoxide to silanes, as well as increased selectivity for the formation of arylsilane products, can be effected by heat activation of the silicon monoxide. The silicon monoxide and catalyst can be combined prior to the activation step, or, the silicon monoxide can be activated first and subsequently combined with the catalyst. Alternatively, the silicon monoxide may be activated during its manufacture. The preferred activation procedure is to combine the silicon monoxide and catalyst prior to the activation step.

The solid silicon monoxide, in particulate form, may be activated by heating at an activation temperature of 50° C. to 1200° C. in an inert atmosphere. The preferred activation temperature range is about 300° C. to about 1100° C. By "about," it is meant any similar temperature which gives comparable silicon monoxide conversion and product selectivity under similar process conditions. In general, an activation time of 0.5 to 20 hours has been found to be useful, when the activation temperature range is 50° C. to 1200° C. Preferred is an activation time of one to 20 hours, when the activation temperature range is 200° C. to 1200° C. More preferred is an activation time of ten to 18 hours, when the activation temperature range is 300° C. to 1100° C.

The silicon monoxide is activated in an environment which has been purged of oxygen. Typically, the silicon monoxide will be activated in the reactor in which it is to be contacted with the aromatic halide. The reactor can be purged of oxygen, for example, by means of a vacuum or an inert purging gas. The purging gas can be any gas which is inert to the solid silicon monoxide. Examples of purging gases are argon, helium, krypton, neon, and nitrogen. Helium and nitrogen are preferred gases for purging.

The silicon monoxide, non-activated or activated, is contacted with catalyst and an aromatic halide at a temperature of 200° C. to 1200° C. to form product silanes. A preferred reaction temperature is about 400° C. to 500° C. By "about," it is meant similar temperatures which give comparable results under comparable process conditions.

Preferred conditions are where an aromatic halide gas is passed through a reactor bed of particulate silicon monoxide, mixed with catalyst, at a rate sufficient to allow product silanes to form. The optimal reaction time for an aromatic halide with silicon monoxide will be dependent upon activation conditions for the silicon monoxide, type of catalyst, reaction temperature, concentration of aromatic halide, and desired conversion of silicon monoxide. In general, reaction times between about four to 50 hours have been found useful. Shorter reaction times may be employed, but with reduced conversion of silicon monoxide. Longer reaction times may also be employed to advantage, depending upon the continuing presence of silicon monoxide in the reactor.

The product silanes as well as excess aromatic halide is collected by standard means, for example, a cold trap. If desired, the excess aromatic halide can be isolated and recycled to the process. The product silanes may be further isolated by standard means, such as chromatography or distillation.

In the described processes, solid silicon monoxide is made to react with the aromatic halide as if the silicon monoxide were an equimolar mixture of reactive silicon and inert silicon dioxide. Therefore, the reactive portion of silicon monoxide represents about 31.85 weight percent of the solid. The spent bed resulting from the described processes can be reactivated by the instant described heat activating process and further conversion of silicon achieved. In addition, unreacted silicon, as well as silicon dioxide, can be recovered and, for example, recycled as feed to a process for making silicon metal or silicon monoxide. The unreacted silicon dioxide may also be used as a filler or filler and reinforcing agent. The unreactive silicon dioxide may be used as a filler, for example, in silicone emulsions or as a filler and reinforcing agent in silicone elastomers.

Product silanes which can be produced by the instant described processes can be, for example, silane ($SiH_4$), and halosilanes, for example, mono-, di-, tri-, and tetra-halosilanes; where the halide is chloride, bromide, iodide, or fluoride. The halosilanes can be, for example, tetrachlorosilane, trichlorosilane, dichlorosilane, chlorosilane, tetrabromosilane, tribromosilane, tetrafluorosilane, trifluorosilane, and mixtures thereof.

The silanes which can be formed by the described processes include arylsilanes. The arylsilanes can be mono-di-, tri-, and tetra-arylsilanes; where the aryl group, R, is an aromatic radical. The radical R can be, for example, phenyl, tolyl, xylyl, or naphthyl. The arylsilanes can be, for example, phenylsilane, diphenylsilane, triphenylsilane, tetraphenylsilane, tolylsilane, ditolylsilane, xylylsilane, naphthylsilane and mixtures thereof.

The silanes which can be formed by the described process include arylhalosilanes. The arylhalosilanes can be, for example, phenylchlorosilane, phenyldichlorosilane, diphenyldichlorosilane, triphenylchlorosilane, phenyltrichlorosilane, phenylbromosilane, phenyldibromosilane, diphenyldibromosilane, phenyltribromosilane, phenyliodosilane, phenyldiiodosilane, phenylflurosilane, phenyldifluorosilane, diphenyldifluorosilane, phenyltrifluorosilane, tolylchlorosilane, tolyldichlorosilane, ditolyldichlorosilane, tolyltrichlorosilane, tolylbromosilane, tolyldibromosilane, ditolyldibromosilane, tolyltribromosilane, tolyliodosilane, tolyldiiodosilane, tolylfluorosilane, tolyldifluorosilane, ditolyldifluorosilane, tolyltrifluorosilane, xylylchlorosilane, xylyldichlorosilane, xylylbromosilane, xylyldibromosilane, xylyliodosilane, xylylfluorosilane, xylyldifluorosilane, naphthylchlorosilane, naphthyldichlorosilane, naphthylbromosilane, naphthylfluorosilane and mixtures thereof.

The preferred silanes produced by the described process are phenyltrichlorosilane and diphenyldichlorosilane.

So that those skilled in the art may better understand the present invention, the following example is offered as illustrative of the instant invention. The example is not intended to be limiting on the processes as described herein. For the following example, all units of parts per million and weight percents are expressed in relation to the total combined weight of catalysts and silicon monoxide, unless otherwise indicated.

EXAMPLE

The product distribution and silicon monoxide conversion of the reaction of solid silicon monoxide (SiO) with chlorobenzene (PhCl) in the presence of various metal catalysts was evaluated in a fixed-bed reactor. The effect of heat activation of the solid silicon monoxide prior to the catalyst reaction was also investigated.

The fixed-bed reactor consisted of a vertical one-inch outer diameter quartz tube. The quartz tube contained at the midpoint a quartz-wool plug for supporting a particulate bed. The reactor was heated in a tube furnace. Feed gases entered at the top of the reactor and flowed downward through the fixed-bed. Product silanes and unreacted feed were collected in a ice water cooled cold trap located at the reactor's exit. The contents of the cold trap were analyzed by gas chromatography.

For each run, particulate silicon monoxide, with a nominal purity of about 99.99 percent, purchased from Cerac Inc. (Milwaukee, WI), was employed. The particle size of the silicon monoxide was less than 325 mesh. A total of 15 grams of silicon monoxide and catalyst mixture were placed in the reactor to form a reactor bed. The metal and metal compounds used in the catalyst mixture are listed in Table 1. The tin catalyst was a powder of grade M #100, with a particle size of 93 to 98 mesh, purchased from Belmont Metals (Brooklyn, NY). The brass catalyst was a brass powder classified as B-126, purchased from U.S. Bronze Powders (Flemington, NJ). The aluminum catalyst was a grade 44 powder with particle size of 20 to 34 micron, purchased from Alcan Powders and Pigments (Union, NJ). The CuCl catalyst was a Type II cuprous chloride powder purchased from Calabrian Chemical (Houston, TX). The $ZnCl_2$ catalyst was a granular analytical reagent grade zinc chloride purchased from Mallinckrodt Inc. (Houston, TX). The $CdCl_2$ catalyst was a cadmium chloride powder with a nominal purity of 99.9% and a particle size of less than 80 mesh, purchased from Cerac Inc. (Milwaukee, WI). The AgCl catalyst was a silver chloride powder with a nominal purity of 99.9% and a particle size of less than 100 mesh, purchased from Cerac Inc. (Milwaukee, WI). A copper and phosphorus alloy (Cu+P) was tested. The composition of the catalyst employed in each run is reported in Table 1.

The silicon monoxide, mixed with the catalysts, was activated by passing helium through the reactor bed at a rate of 10 standard cubic centimeter per minute (sccm) for a period of 15 hours. For Runs 1 through 3, the reactant mixture was activated at an activation temperature of 330° C.; for Runs 4 and 5, the reactant mixture was activated at an activation temperature of 1050° C. After activation of the silicon monoxide and catalyst mixture, vaporized chlorobenzene gas (99.9% analytical reagent grade chlorobenzene, Mallinckrodt Inc., Paris, KY) was passed through the reactor bed at a rate of 2.2 grams per hour. Each of the reactions were run for 21 hours at the reaction temperature reported in Table 1.

The resulting distribution of product silanes from each run are presented in Table 1. The temperature at which the reactant mixture was activated and that at which the reaction was run are reported next to the headings "Activation Temp (°C.)" and "Reaction Temp (°C.)," respectively.

The headings "Sn (ppm)," "Brass (ppm)," "Al (ppm)," and "Cu+P (ppm)" indicate the amount of tin, brass, aluminum, and copper-phosphorus alloy catalyst, in respective order, in unit of parts per million of the total combined weight of the silicon monoxide and catalyst mixture, used in each run. The headings "CuCl (wt %)," "ZnCl$_2$ (wt %)," "CdCl$_2$ (wt %)" and "AgCl (wt %)" indicate the amount of cuprous chloride, zinc chloride, cadmium chloride, and silver chloride catalysts, respectively, in weight percent of the total weight of the silicon monoxide and catalyst mixture, used in each run. The heading "Total (wt %)" indicates the total concentration of the catalysts in the reactor bed, in weight percent of the total combined weight of silicon monoxide and catalyst mixture. The headings "HSiCl$_3$ (wt %)," "SiCl$_4$ (wt %)," "PhSiCl$_3$ (wt %)" and "Ph$_2$SiCl$_2$ (wt %)" indicate the amount of trichlorosilane, tetrachlorosilane, phenyltrichlorosilane and diphenyldichlorosilane, respectively, produced by the process.

The percent conversion of the available silicon, "Si Conv (%)," to silanes was calculated. By the described process, solid silicon monoxide reacts as if it were an equimolar mixture of reactive silicon and inert silicon dioxide. Therefore the reactive portion of SiO represents 31.85 weight percent of the solid. For this reason, conversions of the solid silicon monoxide are expressed as the percentage of available silicon converted to silane products. The percent conversion values were calculated as: Si Conv (%)=100×(Si in products (g)/(0.3185×SiO added to reactor(g)).

Product selectivity of the reaction was calculated directly from the amounts of each silane product formed in proportion to the percent total product formed, as determined by chromatographic analysis. That is: Selectivity (wt %)=100×(specific product formed (g)/total silane product (g)).

TABLE 1

Reaction of Activated Silicon Monoxide with Chlorobenzene in the Presence of Metal Catalysts

| | Run 1 | Run 2 | Run 3 | Run 4 | Run 5 |
|---|---|---|---|---|---|
| Activation Temp (°C.) | 330 | 330 | 330 | 1050 | 1050 |
| Reaction Temp (°C.) | 480 | 480 | 500 | 480 | 480 |
| CATALYSTS | | | | | |
| Sn (ppm) | — | — | 68 | — | — |
| Brass (ppm) | — | — | 670 | — | — |
| Al (ppm) | 1440 | 1495 | 1675 | 1752 | 1513 |
| Cu + P (ppm) | — | — | 2230 | — | — |
| CuCl (wt %) | 10.0 | 15.0 | 25.0 | 25.0 | 15.0 |
| ZnCl$_2$ (wt %) | 2.3 | 4.9 | 14.6 | — | — |
| CdCl$_2$ (wt %) | 1.9 | — | — | — | — |
| AgCl (wt %) | — | — | — | 10.0 | 5.0 |
| Total (wt %) | 14.4 | 20.1 | 40.1 | 35.2 | 20.1 |
| Si Conv (%) | 3.7 | 10.5 | 18.2 | 27.2 | 11.9 |
| SELECTIVITY | | | | | |
| HSiCl$_3$ (wt %) | 1.3 | 6.0 | 2.5 | 0.6 | 0.5 |
| SiCl$_4$ (wt %) | 83.0 | 69.2 | 67.1 | 13.3 | 11.0 |
| PhSiCl$_3$ (wt %) | 15.2 | 24.6 | 29.8 | 72.9 | 69.5 |
| Ph$_2$SiCl$_2$ (wt %) | 0.5 | 0.3 | 0.7 | 13.3 | 19.1 |

The data presented in Table 1 indicate the variety of catalyst compositions effective for facilitating the reaction of solid silicon monoxide with aromatic halides to form silanes. Results presented in Table 1 also show that a higher selectivity for phenylchlorosilane products can be obtained when reactants are heat activated.

What is claimed is:

1. A process for preparing silanes, the process comprising:
   (A) contacting solid silicon monoxide, an aromatic halide of formula

RX, where X is a halide and R is selected from a group consisting of aryl radicals, and a catalyst effective in facilitating reaction of the solid silicon monoxide with the aromatic halide; at a reaction temperature of 200° C. to 1200° C.; and
   (B) forming silanes of formula $H_a R_b SiX_{4-a-b}$ where a is an integer from 0 to 4, b is an integer from 0 to 4, a+b is an integer from 0 to 4, and R and X are as previously described.

2. A process according to claim 1, where the aryl radical is selected from a group consisting of phenyl, tolyl, xylyl, and naphthyl radicals.

3. A process according to claim 1, where the halide is selected from a group consisting of chloride, bromide, iodide, and fluoride.

4. A process according to claim 1, where the aromatic halide is chlorobenzene.

5. A process according to claim 1, where the reaction temperature is about 400° C. to 500° C.

6. A process according claim 1, where the catalyst is selected from a group consisting of aluminum and aluminum compounds, antimony and antimony compounds, copper and copper compounds, cadmium and cadmium compounds, iron and inorganic iron compounds, manganese and manganese compounds, mercury and mercury compounds, nickel and nickel compounds, silver and silver compounds, tin and tin compounds, zinc and zinc compounds, phosphorous, metal phosphides, metal phosphorous alloys and mixtures thereof.

7. A process according to claim 6, where the catalyst is selected from a group consisting of aluminum and aluminum compounds, copper and copper compounds, silver and silver compounds, tin and tin compounds, zinc and zinc compounds and mixtures thereof.

8. A process according to claim 7, where the catalyst is selected from a group consisting of Al, AgCl, CuCl and mixtures thereof.

9. A process according to claim 6, where the catalyst is present at a level of 10 to 40 weight percent of the combined catalyst and silicon monoxide weight.

10. A process according to claim 1, further comprising heat activating the silicon monoxide in contact with the catalyst in an inert atmosphere, at an activation temperature of 200° C. to 1200° C., for an activation time of one to 20 hours, prior to contact with the aromatic halide.

11. A process according to claim 10, where the activation temperature is about 300° C. to 1100° C.; the activation time is 10 to 18 hours; and the reaction temperature is 400° C. to 500° C.

12. A process according to claim 10, where the inert atmosphere is a gas selected from a group consisting of nitrogen and helium.

13. A process according to claim 10, where the aryl radical is selected from a group consisting of phenyl, tolyl, xylyl, and naphthyl radicals.

14. A process according to claim 10, where the halide is selected from a group consisting of chloride, bromide, iodide, and fluoride.

15. A process according to claim 10, where the aromatic halide is chlorobenzene; and the inert atmosphere is helium.

16. A process according claim 10, where the catalyst is selected from a group consisting of aluminum and aluminum compounds, antimony and antimony compounds, copper and copper compounds, cadmium and cadmium compounds, iron and inorganic iron compounds, manganese and manganese compounds, mercury and mercury compounds, nickel and nickel compounds, silver and silver compounds, tin and tin compounds, zinc and zinc compounds, phosphorous, metal phosphides, metal phosphorous alloys and mixtures thereof.

17. A process according to claim 16, where the catalyst is selected from a group consisting of aluminum and aluminum compounds, copper and copper compounds, silver and silver compounds, tin and tin compounds, zinc and zinc compounds and mixtures thereof.

18. A process according to claim 17, where the catalyst is selected from a group consisting of Al, AgCl, CuCl and mixtures thereof.

19. A process according to claim 16, where the catalyst is present at a level of 10 to 40 weight percent of the combined catalyst and silicon monoxide weight.

20. A process according to claim 1, where unreacted silicon monoxide and catalyst present at the end of a run is reactivated by heating in an inert atmosphere, at an activation temperature of 200° C. to 1200° C., for an activation time of one to 20 hours, prior to contact with the aromatic halide.

21. A process according to claim 10, where the silanes are selected from a group consisting of phenyltrichlorosilane, diphenyldichlorosilane, and mixtures thereof.

22. A process according to claim 1, further comprising heat activating the silicon monoxide in an inert atmosphere, at an activating temperature of 200° C. to 1200° C., for an activation time of one to 20 hours, prior to contact with the catalyst and the aromatic halide.

* * * * *